(12) United States Patent
Linder et al.

(10) Patent No.: US 12,169,186 B2
(45) Date of Patent: Dec. 17, 2024

(54) METHOD AND ARRANGEMENT FOR CRACK DETECTION AT AN EDGE IN A METALLIC MATERIAL

(71) Applicant: ABB Schweiz AG, Baden (CH)

(72) Inventors: Sten Linder, Trosa (SE); Ulf Lifvenborg, Västerås (SE)

(73) Assignee: ABB Schweiz AG, Baden (CH)

( * ) Notice: Subject to any disclaimer, the term of this patent is extended or adjusted under 35 U.S.C. 154(b) by 195 days.

(21) Appl. No.: 18/002,191

(22) PCT Filed: Jun. 14, 2021

(86) PCT No.: PCT/EP2021/065988
§ 371 (c)(1),
(2) Date: Dec. 16, 2022

(87) PCT Pub. No.: WO2021/254969
PCT Pub. Date: Dec. 23, 2021

(65) Prior Publication Data
US 2023/0243779 A1      Aug. 3, 2023

(30) Foreign Application Priority Data

Jun. 16, 2020 (EP) ..................................... 20180392

(51) Int. Cl.
*G01N 27/82* (2006.01)
*G01N 27/90* (2021.01)
(Continued)

(52) U.S. Cl.
CPC ......... *G01N 27/82* (2013.01); *G01N 33/2045* (2019.01); *G01N 27/9026* (2013.01); *G01N 27/9046* (2013.01)

(58) Field of Classification Search
CPC ........ G01N 27/00; G01N 27/72; G01N 27/82; G01N 27/90; G01N 27/9013;
(Continued)

(56) References Cited

U.S. PATENT DOCUMENTS 3,978,396 A * 8/1976 Inouye ................... G01V 3/105
324/337
4,792,755 A * 12/1988 Hüschelrath ........... G01N 27/82
324/225
(Continued)

FOREIGN PATENT DOCUMENTS

EP         2574911 A1    4/2013
EP         2574912 A1    4/2013
(Continued)

OTHER PUBLICATIONS

Extended European Search Report; Application No. 20180392.1; Completed: Nov. 23, 2020; Issued: Dec. 2, 2020; 34 Pages.
(Continued)

*Primary Examiner* — Hoai-An D. Nguyen
(74) *Attorney, Agent, or Firm* — Whitmyer IP Group LLC

(57) ABSTRACT

The invention relates to a method of determining a crack at an edge of a metallic material, the edge having a curvature with a radius. The method including:
  feeding and controlling a current to a transmitter coil for generating a magnetic field in the metallic material,
  detecting the magnetic field by means of a receiver coil, which detected magnetic field thereby generates a signal) in the receiver coil,
  determining first, second and third signal values of the signal at a first time, a second time and a third time, respectively,
(Continued)

determining a possible presence of a crack and its crack depth based on the first, second and third signal values by means of determining a characteristic relation between the signal values.

18 Claims, 4 Drawing Sheets

(51) Int. Cl.
*G01N 27/9013* (2021.01)
*G01N 33/2045* (2019.01)

(58) Field of Classification Search
CPC ........... G01N 27/9026; G01N 27/9046; G01N 33/00; G01N 33/20; G01N 33/204; G01N 33/2045
USPC ................ 324/323, 326, 329, 200, 228, 239
See application file for complete search history.

(56) References Cited

U.S. PATENT DOCUMENTS

| | | |
|---|---|---|
| 5,391,988 A | 2/1995 | Kitagawa |
| 5,451,872 A | 9/1995 | Antonine et al. |
| 6,377,040 B1 | 4/2002 | Hell |
| 6,486,673 B1 * | 11/2002 | Goldfine ................ G01V 3/088 |
| | | 324/688 |
| 7,626,383 B1 * | 12/2009 | Sun ......................... G01N 27/82 |
| | | 324/242 |
| 7,772,839 B2 * | 8/2010 | Watson ................... G01D 5/202 |
| | | 324/228 |
| 10,984,946 B2 * | 4/2021 | Percebon .............. H01F 27/366 |
| 2005/0237055 A1 * | 10/2005 | Sun .......................... G01N 27/82 |
| | | 324/240 |
| 2006/0290349 A1 * | 12/2006 | Na ...................... G01N 27/9006 |
| | | 324/228 |
| 2007/0285088 A1 | 12/2007 | Meilland |

FOREIGN PATENT DOCUMENTS

| | | |
|---|---|---|
| JP | 59226860 A | 12/1984 |
| JP | 11326284 A | 11/1999 |
| JP | 2001099816 A | 4/2001 |
| JP | 3267754 B2 | 3/2002 |
| JP | 2013076700 A | 4/2013 |
| JP | 2017096876 A | 6/2017 |

OTHER PUBLICATIONS

International Preliminary Report on Patentability; Application No. PCT/EP2021/065988; Issued: Sep. 23, 2022; 17 Pages.
International Search Report and the Written Opinion of the International Searching Authority; Application No. PCT/EP2021/065988; Completed: Sep. 9, 2021; Mailing Date: Sep. 17, 2021; 16 Pages.
Written Opinion of the International Preliminary Examining Authority; Application No. PCT/EP2021/065988; Issued: May 17, 2022; 5 Pages.
Japanese Office Action; Application No. 2022-576145; Completed: Oct. 24, 2023; Mailing Date: Oct. 31, 2023; 4 Pages.

* cited by examiner

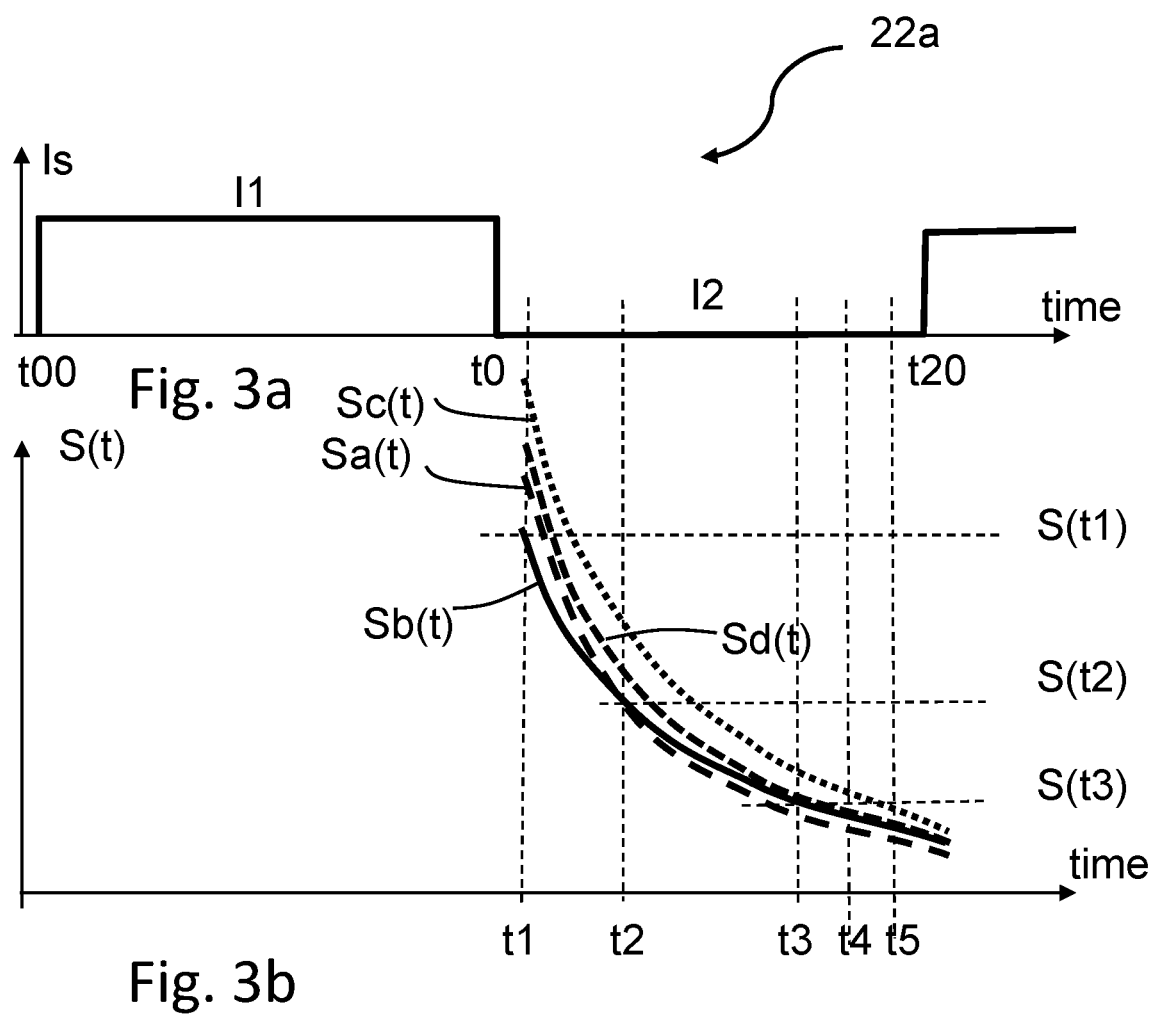

METHOD AND ARRANGEMENT FOR CRACK DETECTION AT AN EDGE IN A METALLIC MATERIAL

FIELD OF THE INVENTION

The present disclosure generally relates to quality inspection of a metallic material, and in particular to crack detection at an edge of a metallic material utilising electromagnetic induction.

BACKGROUND OF THE INVENTION

A known method of contactless crack measurements of a metallic material is to utilise optical means. The metallic material may be irradiated by light wherein a crack may be detected by means of an optical sensor such as a camera. Drawbacks with optical methods are that it is not possible to detect cracks which are not visible on the surface of the metallic material, and that colour variations in the metallic material may be interpreted as cracks by the optical sensor. Optical methods have been proved to be difficult to use in other applications than for inspection of completely clean and smooth metal surfaces.

Inspection of metallic materials in for instance steel production has been made utilising inductive techniques. When using an inductive technique, a current is induced in the metallic material, e.g. a slab or a metal sheet, by means of a time-varying magnetic field generated by a transmitter coil fed with a likewise time-varying current. When the induced current encounters a crack in the metallic material, the crack constitutes an obstacle to the induced current. As a result, the crack alters the induced current at the crack as compared to a metallic material without a crack. The altered current provides a change in the magnetic field around the current. The change in the magnetic field is measured by a receiver coil, whereby it can be determined that a crack is present in the inspected surface portion of the metallic material. Such inspection of a metallic material is e.g. disclosed in EP2574911.

There are several drawbacks with the induction techniques used today for crack detection in metallic materials. For example, close to the edge or corner of the metallic material to be measured, the curvature of the edge or a sudden positional change of the edge relative the coils can be mistaken for a crack. Due to the fact that it is difficult to keep such influencing parameters constant, it has been difficult to use inductive techniques for crack inspection of irregular surfaces such as casted metallic surfaces.

There is thus a need in the industry for providing an improved method and arrangement for crack detection at an edge in a metallic material.

SUMMARY

An object of the present invention is to overcome at least some of the above problems, and to provide a solution for detection of cracks at the edge of the metallic material which, at least to some extent, is improved compared to prior art solutions. This, and other objectives, which will become apparent in the following are accomplished by means of a method of determining a crack at an edge of a metallic material, and arrangement for determining a crack at an edge of a metallic material.

According to a first aspect of the present invention, a method of determining a crack at an edge of a metallic material, the edge having a curvature with a radius, is provided. The method comprising the steps of:

S10: feeding a current with a first magnitude to a transmitter coil for generating a magnetic field in the metallic material, S20: controlling the current such that it obtains a second magnitude when the magnetic field is estimated to have penetrated deeper than a deepest crack depth desired to be measured in the metallic material, S30: detecting the magnetic field by means of a receiver coil, which detected magnetic field thereby generates a signal in the receiver coil, S40: determining a first signal value of the signal at a first time at which it has been estimated that any disturbances due to control of the current to obtain the second magnitude have ceased, and S50: determining a second signal value of the signal at a second time after the first time, and S60: determining a third signal value of the signal at a third time after the second time, and S70: determining a possible presence of a crack and its crack depth based on the first, second and third signal values by means of determining a characteristic relation between at least two of the following combinations of signal values: the first signal value and the second signal value; the second signal value and the third signal value; and the first signal value and the third signal value, wherein the characteristic relation between the least two combinations of signal values are independent of the position of the edge and the radius of the curvature of the edge.

By determining characteristic relation between the least two combinations of signal values according to the above specified time, a crack depth may be determined independently of the position of the edge and the radius of the curvature of the edge, without having other process parameters affecting the determined crack depth value. Thus, it should be understood that the characteristic relation between the least two combinations of signal values are independent of the position of the edge and the radius of the curvature of the edge. Hence reliable crack depth measurements may be provided at the edge of the metallic material.

For example, at least small cracks (typically <3 mm crack depth) which are particularly difficult to differentiate from variations in the radius of the edge are detectable and measurable by applying the above specified method. It should be understood that the method may be carried out by feeding the first current with a first magnitude to the transmitter coil during a first time interval, and controlling the current such that it obtains a second magnitude during a second time interval, repeatedly. The first, second and third signal values are all measured during the second time interval in which the current is controlled to obtain the second magnitude.

According to at least one example embodiment, the detecting of the magnetic field by means of the receiver coil is embodied by detecting magnetic field changes (i.e. induced voltage or dB/dt). Furthermore, it should be noted that the "at a first time at which it has been estimated that any disturbances due to control of the current to obtain the second magnitude have ceased" is at least partly related to a voltage peak (dB/dt) caused by the portion of the magnetic field which does not penetrate into the metallic material. In other words, this voltage peak (dB/dt) should have ceased at the first time.

According to at least one example embodiment, the first time is additionally determined at which a current induced in the metallic material due to control of the current to obtain the second magnitude has penetrated deeper in the metallic material than a depth corresponding to surface irregularities of the metallic material and crack depths not desired to be measured.

Thus, the method is independent of the surface irregularities. According to at least one example embodiment, the method further comprises the step of providing the transmitter coil at least partly outside of the edge of the metallic material.

Hereby, induced currents can be concentrated to the edge of the metallic material, enabling crack determination in this area. The receiver coil may according to at least one example embodiment be arranged such that its magnetic center is arranged inside of the edge of the metallic material.

According to at least one example embodiment, the step comprises providing the transmitter coil at least partly inside of the edge of the metallic material. Thus, the transmitter coil may be arranged to overlap the edge of the metallic material, facilitating crack determination. According to at least one example embodiment, the ratio of the portion of the transmitter coil arranged outside of the edge to the portion of the transmitter coil arranged inside of the edge is between 0.1-0.4. It should be understood that any overlap of the edge is referring to an overlap in a plane parallel to the surface of the metallic material.

According to at least one example embodiment, the third time is a time at which it has been estimated that any influence of a radius change of the curvature of the edge has ceased.

Hereby, the characteristic relation of two signal values, wherein at least one is based on the third time, will be independent of the radius of the curvature of the edge.

According to at least one example embodiment, the method further comprises the steps of:
    establishing an edge position parameter based on the position of the edge relative a reference position
    establishing a radius parameter based on the radius of the curvature of the edge,
wherein said characteristic relations are independent of the edge position parameter and the radius parameter.

By specifying such parameters, independence of edge characteristics, as the edge position and radius of the curvature of the edge, is simplified and easily integrated into an algorithm used for determining the presence of the crack and its crack depth. The reference position may e.g. be the magnetic axis of the receiver coil. Edge position may include both horizontal and vertical distance to the edge relative the reference position, alternatively only the horizontal distance. Thus, and according to at least one example embodiment, the edge position parameter represents, or corresponds to, the position of the edge relative a reference position, and the radius parameter represents, or corresponds to, the radius of the curvature of the edge.

According to at least one example embodiment, the step of determining a possible presence of a crack and its crack depth comprises comparing the characteristic relations with corresponding reference signals.

Hereby, comparison is made with a metallic material with known characteristics (edge position, radius of the curvature of the edge, and non-presence of cracks). In more detail, the characteristic relations formed which are independent of the edge position and the radius of the curvature of the edge, are compared with corresponding characteristic relations for a metallic material having no cracks.

According to at least one example embodiment, the method further comprises the steps of:

establishing a first reference signal for a metallic material with a crack, and with a first radius reference value of the radius parameter and a first edge reference value of the edge position parameter;
establishing a second reference signal for a metallic material having no cracks, and with the first radius reference value of the radius parameter and the first edge reference value of the edge position parameter;
establishing a third reference signal for a metallic material having no cracks, and with said first radius reference value, and a predetermined change of the edge position parameter relative the first edge reference value;
establishing a fourth reference signal for a metallic material having no cracks, and with said first edge reference value, and a predetermined change of the radius parameter relative the first radius reference value.

Hereby, the change characteristics of the edge, at least the edge position and the radius of the curvature of the edge, can be determined and at least the first, second and/or third times can be chosen based on the determined change characteristics. For example, the third time can be determined as a time which the influence of a radius change of the curvature of the edge has ceased.

Moreover, the measured signal, or measured signals, based on at least steps S10, S20, S30, S40, S50 and S60, or the determining in step S70, can be compared with reference signals corresponding to a metallic material having no crack at the edge.

Thus, according to at least one example embodiment, the step of determining a possible presence of a crack and its crack depth comprises using the characteristic relations with corresponding signal values of the first, second, third and/or fourth reference signal.

According to at least one example embodiment, the first, second and third times are separate points in time.

The separate points in time are based on elapsed time from the initialization of controlling the current such that it obtains a second magnitude. Alternatively, the first, second and third times are respective short time ranges spanning from −30% to +30% of the respective point in time. For example, the first, second and third times or time ranges do not overlap, and/or do not share a common starting or ending time.

According to at least one example embodiment, in the step of feeding, the current is essentially constant.

According to at least one example embodiment, the estimation of the magnetic field having penetrated deeper than a deepest crack depth desired to be measured in the metallic material is based on when the feeding the current to the transmitter coil starts, a deepest crack depth desired to be measured and the relative permeability and electrical resistivity of the metallic material.

According to at least one example embodiment, the first time is estimated based on a time when control of the current to obtain its second magnitude starts and on a relation between the relative permeability and electrical resistivity of the metallic material, and/or based on the time when the current obtains its second magnitude, the deepest crack depth desired to be measured and the relative permeability and electrical resistivity of the metallic material. The first time may e.g. be 100 µs or between 100 µs and 700 µs, such as e.g. between 100 µs and 500 µs.

According to at least one example embodiment, the first, second and/or third signal value is a respective single signal value, a mean signal value or an integration of the signal during said short time ranges over the first, second and third time, respectively.

According to at least one example embodiment, said receiver coil is a first receiver coil and the method further comprising the steps of:
- detecting the magnetic field by means of a second receiver coil, which detected magnetic field thereby generates a signal in the second receiver coil, and
- determining the position of the edge and the distance from a surface of the metallic material, relative the first and second receiver coils, respectively.

Hereby, the coil arrangement (i.e. the transmitter coil, and the first and second receiver coils) and its distance relative the edge and the surface of the metallic material can be determined. Such positioning information can be used e.g. in combination with a positioning arrangement configured to horizontally and vertically re-position the coil arrangement, in order to e.g. keep a constant distance between the coil arrangement and the edge, and between the coil arrangement and the surface of the metallic material, respectively.

According to a second aspect of the present invention, an arrangement for determining a crack at an edge of a metallic material, the edge having a curvature with a radius, is provided. The arrangement comprising:
- a transmitter coil arranged to generate a magnetic field in the metallic material,
- a receiver coil arranged to detect the magnetic field,
- a signal generator arranged to feed a current having a first magnitude to the transmitter coil for generating the magnetic field in the metallic material,
- a control unit arranged to control the signal generator such that the current obtains a second magnitude when the magnetic field is estimated to have penetrated deeper than a deepest crack depth desired to be measured in the metallic material, and
- a computing arrangement arranged to receive a signal created by the magnetic field detected by the receiver coil, and to determine a first signal value of the signal at a first time at which it has been estimated that any disturbances due to control of the current to obtain the second magnitude have ceased,
- the computing arrangement being further arranged to determine a second signal value of the signal at a second time after the first time, and to determine a third signal value of the signal at a third time after the second time, wherein the computing arrangement is further arranged to determine a possible presence of a crack and its crack depth based on the first, second and third signal values by means of determining a characteristic relation between at least two of the following combinations of signal values: the first signal value and the second signal value; the second signal value and the third signal value; and the first signal value and the third signal value.

Effects and features of the second aspect of the invention are largely analogous to those described above in connection with the first aspect of the invention. Embodiments mentioned in relation to the first aspect of the invention are largely compatible with the second aspect of the invention, of which some are exemplified below.

According to at least one example embodiment, the transmitter coil is, in operation, configured to be arranged at least partly outside of the edge of the metallic material.

Hereby, induced currents can be concentrated to the edge of the metallic material, enabling crack determination in this area. The receiver coil may according to at least one example embodiment be, in operation, configured to be arranged such that its magnetic center is arranged inside of the edge of the metallic material.

According to at least one example embodiment, the transmitter coil is, in operation, configured to be arranged at least partly inside of the edge of the metallic material.

Thus, the transmitter coil may, in operation, be configured to be arranged to overlap the edge of the metallic material, facilitating crack determination. According to at least one example embodiment, the ratio of the portion of the transmitter coil configured to be arranged outside of the edge to the portion of the transmitter coil configured to be arranged inside of the edge is between 0.1-0.4.

According to at least one example embodiment, the computing arrangement is arranged to determine the third signal value at the third time being a time at which it has been estimated that any influence of a radius change of the curvature of the edge has ceased.

According to at least one example embodiment, the computer arrangement is arranged to determine the first time, additionality to the criteria mentioned above, at which a current induced in the metallic material due to control of the current to obtain the second magnitude has penetrated deeper in the metallic material than a depth corresponding to surface irregularities of the metallic material and crack depths not desired to be measured.

According to at least one example embodiment, the computing arrangement is arranged do determined the first signal value, the second signal value and the third signal value at the first time, the second time and the third time, respectively, wherein the first, second and third times are separate points in time.

As mentioned in relation to the first aspect of the present invention, the separate points in time are based on elapsed time from the initialization of the control unit to control the signal generator such that the current obtains a second magnitude. Alternatively, the first, second and third times are respective short time ranges spanning from −30% to +30% of the respective point in time. For example, the first, second and third times or time ranges do not overlap, and/or do not share a common starting or ending time.

According to at least one example embodiment, said receiver coil is a first receiver coil, and the arrangement further comprises a second receiver coil arranged to detect the magnetic field, wherein the computing arrangement is further configured to receive a signal created by the magnetic field detected by the second receiver coil, and configured to determine the position of the edge and the distance from a surface of the metallic material, relative the first and second receiver coils, respectively.

According to at least one example embodiment, the arrangement comprises a positioning arrangement configured to adjust the position of the transmitter coil, the first receiver coil, and/or the second receiver coil. The determined position of the edge and the distance from a surface of the metallic material, relative the first and second receiver coils, respectively, may be used as input to the positioning arrangement. The positioning arrangement may e.g. be configured to keep such position and distance constant.

It should be understood that for both the first and second aspects of the invention, the distance from the edge to the first receive coils (or any reference position within the coil arrangement or crack detecting arrangement) is typically a horizontal distance, i.e. a distance parallel to a horizontal surface, e.g. the surface of the metallic material. Correspondingly, the distance from a surface of the metallic material, relative the second receiver coils, is a vertical distance perpendicular to the horizontal distance.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

BRIEF DESCRIPTION OF THE DRAWINGS

These and other aspects of the present inventive concept will now be described in more detail, with reference to the appended drawings showing an example embodiment of the inventive concept, wherein:

FIGS. 3a and 3b show diagrams of first, second, and third times for determining characteristic relations of signals e.g. detected by the arrangement in FIG. 1 or FIGS. 2a and 2b.

DETAILED DESCRIPTION OF EXAMPLE EMBODIMENTS

In the following description, for purposes of explanation and not limitation, specific details are set forth such as particular components, interfaces, techniques, etc. in order to provide a thorough understanding of the present invention. However, it will be apparent to those skilled in the art that the present invention may be practiced in other embodiments that depart from these specific details. In other instances, detailed descriptions of well known devices, circuits, and methods are omitted so as not to obscure the description of the present invention with unnecessary detail.

The arrangement presented herein is adapted to detect cracks at an edge in a metallic material by determining the crack depth of a crack. Advantageously, the arrangement may be used under extreme conditions, for instance in a metal making process such as during casting or a rolling process. The arrangement may in particular be used for accurate crack depth measurement of cracks on rough metallic surfaces.

Any metallic material which has a conductivity which is high enough to allow a current to be induced in the metallic material may be inspected by means of the methods and arrangements presented herein, e.g. steel.

Figure 1:
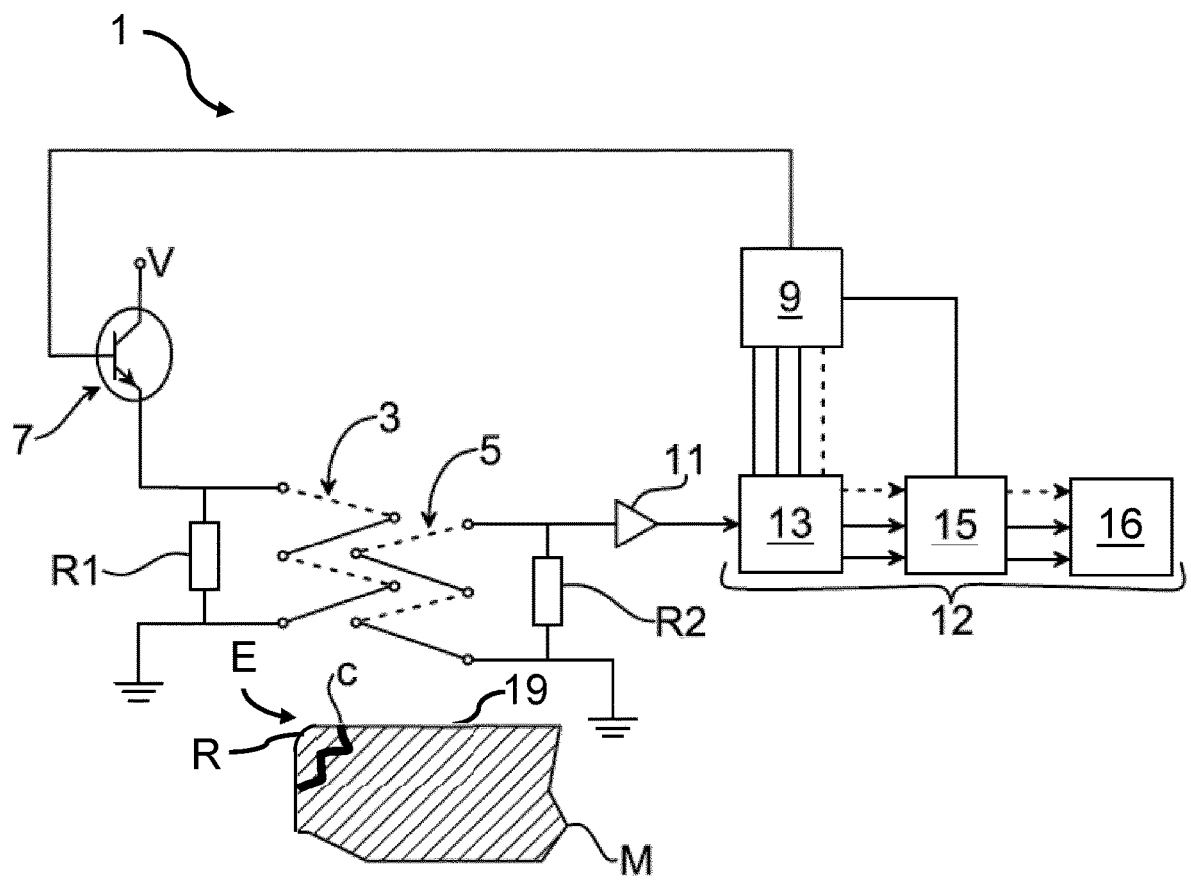
FIG. 1 is a schematic view of an example of an arrangement for crack detection in a metallic material.
Figure 2A:
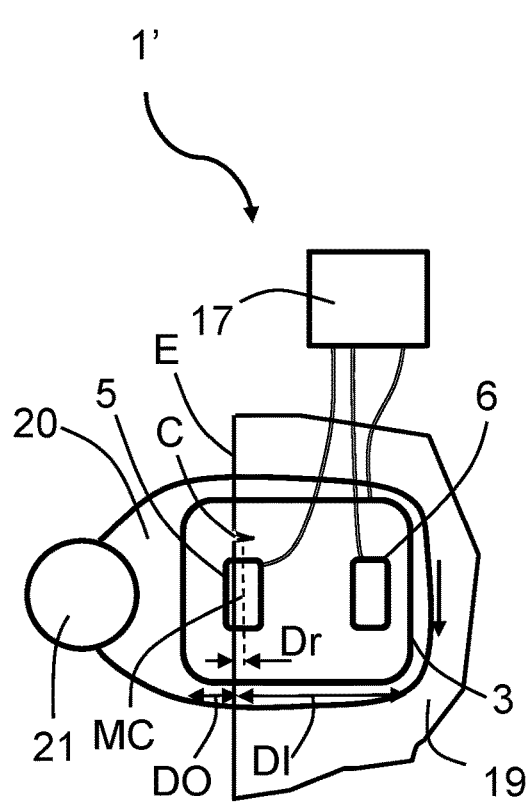
FIGS. 2a and 2b are schematic views of an example of an arrangement for crack detection in a metallic material.

FIG. 1 shows a schematic view of an example of an arrangement 1 for detecting cracks in a surface 19 at an edge E of a metallic material M. The edge E runs along the metallic material M in the longitudinal direction, or direction of movement of the metallic material M, as can be seen in FIG. 2a. The edge E has a curvature with a radius R, which may be curved as in FIG. 1, or edgy. Arrangement 1 comprises signal generator 7 arranged to generate an output signal, a control unit 9 arranged to control the output signal of the signal generator 7, a transmitter coil 3 arranged to receive the output signal from the signal generator 7 to thereby generate a magnetic field in a metallic material M which is to be inspected for cracks, a first resistor R1, a receiver coil 5 arranged to detect the magnetic field and to create a signal based on the detected magnetic field, a second resistor R2, an amplifier 11 arranged to amplify the signal from the receiver coil 5, and a computing arrangement 12 arranged to process the signal from the amplifier 11 in order to determine whether a crack C is present in the metallic material M at the edge E by determining a possible crack depth CD. The computing arrangement 12 may comprise various subunits such as a first unit 13, a second unit 15, and a third unit 16.

In general, the present disclosure involves the generation of a magnetic field in the metallic material M at the edge E, detecting the magnetic field, and determining characteristic relations of signals pertaining to the detected magnetic field at certain predetermined times, to thereby be able to determine a crack depth, as will be detailed in the following.

Figure 2B:
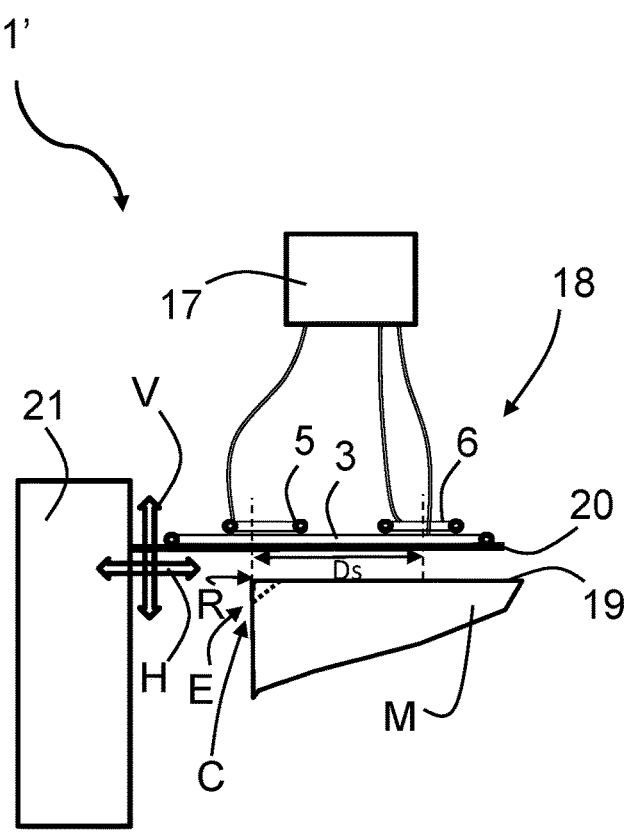

FIGS. 2a and 2b show schematic views of another example of an arrangement 1' for detecting cracks in a surface 19 at and edge E of a metallic material M. FIG. 2a is a top view and FIG. 2b is a side view. Arrangement 1' of FIGS. 2a and 2b is in principle the same as arrangement 1 of FIG. 1, why mainly the differences between the arrangements are described in the following. For example, the signal generator 7, the control unit 9, the amplifier 11 and the computing arrangement 12 are commonly incorporated in component 17 in FIGS. 2a and 2b, but will be referred to as visualized in FIG. 1 in the following. The arrangement 1' comprises the transmitter coil 3 and a first receiver coil 5 having the same functionality as described with reference to FIG. 1. Moreover, the arrangement 1' comprises a second receiver coil 6 arranged distant to the first receiver coil 5. The transmitter coil 3, the first and second receiver coils 5, 6 are here commonly referred to as a coil arrangement 18. Even further, the arrangement 1' comprises a platform 20 to which the coil arrangement 18 are connected and movable with. The platform 20 is coupled to a positioning arrangement 21 configured to adjust the position of the coil arrangement 18, both vertically V and horizontally H, as indicated in FIG. 2b. It should be noted that the platform 20 is not needed for being able to re-position the coil arrangement 18, but that each of the transmitter coil 3, the first receiver coil 5 and the second receiver coil 6 may be directly coupled to the positioning arrangement 21. It should be noted that the first and second resistors R1, R2 shown in FIG. 1 are omitted in FIGS. 2a and 2b for increased comprehensibility, but may be considered to be integrated in the transmitter coil 3 and first receiver coil 5, respectively, or in platform 20. Correspondingly, the second receiver coil 6 may be assumed to be connected in parallel to a third resistor R3 in the same way as the first receiver coil 5 is connected to the second resistor R2, such third resistor may be integrated into second receiver coil 6 or the platform 20.

Figure 4:
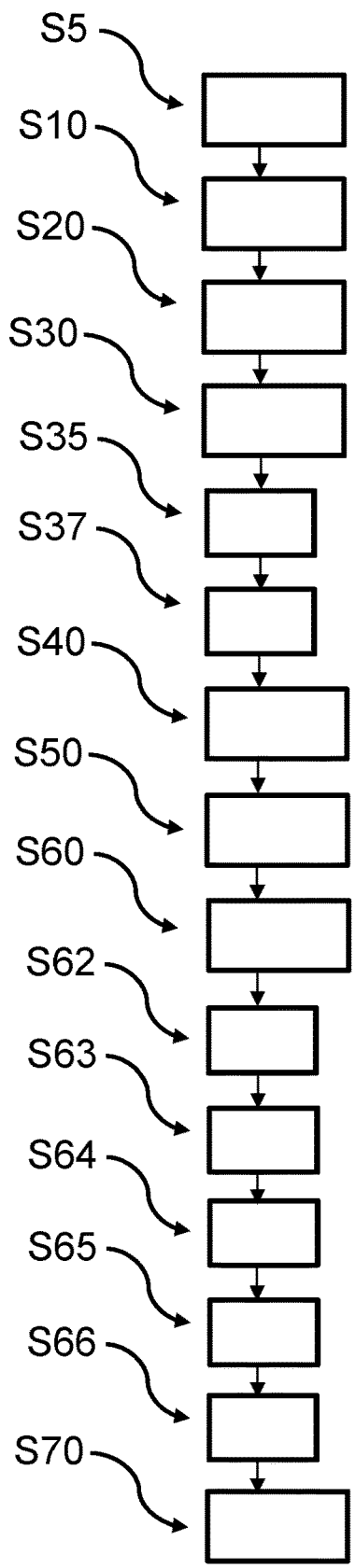
FIG. 4 is a flowchart of methods of determining a crack depth at an edge of a metallic material.

Examples of the operation of the arrangement 1' will now be described in more detail with reference to FIGS. 2-4. The metallic material M, for instance a slab or a metal sheet, which is to be inspected for cracks C, is placed in the vicinity of the transmitter coil 3 and the first and second receiver coils 5, 6. More specifically, the arrangement 1' is arranged such that the transmitter coil 3 arranged at least partly outside of the edge E, indicated by the distance DO, and at least partly inside of the edge E, indicated by the distance DI. The ratio of DO/DI is preferably between 0.1 and 0.4. The first receiver coil 5 is in FIGS. 2a and 2b arranged to partly overlap the edge E, such that its magnetic center MC is arranged inside of the edge E. The second receiver coil 6 is in FIGS. 2a and 2b fully arranged inside of the edge E, and over the metallic material M. Typically the respective magnetic axis of the transmitter coil 3, and the first and second receiver coils 5, 6 are perpendicular to the surface 19 of the metallic material M. Preferably, each one of the transmitter coil 3, and first and second receiver coils 5, 6 is a flat coil with a minor propagation along its magnetic axis compared to perpendicularly to its magnetic axis. The metallic material M typically move in relation to the coil arrangement 18 during crack inspection to thereby enable inspection along the surface 19 of the metallic material M. and specifically at the edge E of the metallic material M. As described above, the transmitter coil 3 may be arranged at least partly outside of the edge E. Thus, in a step S5 preceding the first step S10 present below, the transmitter coil 3 is provided at least partly outside of the edge E of the metallic material M. In this step, S5, the transmitter coil 3 may additionally be provided at least partly inside of the edge E of the metallic material M.

The control unit 9 (only shown in FIG. 1, incorporated into component 17 of FIGS. 2a and 2b) is arranged to provide a control signal to the signal generator 7 (only shown in FIG. 1, incorporated into component 17 of FIGS. 2a and 2b) to thereby control the output signal, e.g. a current, of the signal generator 7 provided to the transmitter coil 3. The signal generator 7 may for instance comprise a transistor which may be controlled by the control unit 9 to be in an open state and thereby provide a current to the transmitter coil 3 or a closed state in which it does not provide a current to the transmitter coil 3. In one embodiment the control unit 9 is arranged to control the signal generator 7 such that the signal generator generates a current which is essentially constant having a first magnitude I1 in a first time span t00-t0, as shown in FIG. 3a.

In a first step S10 the current with the first magnitude I1 is fed to the transmitter coil 3. A magnetic field is thereby created in the metallic material M at the edge E. During crack inspection, the surface 19 of the metallic material M is arranged sufficiently close to the transmitter coil 3 such that the magnetic field around the transmitter coil 3 is able to penetrate into the metallic material M thus causing the magnetic field in the metallic material M. The distance may e.g. be 10-25 mm, e.g. 10-15 mm or 15-25 mm.

At a point in time t0 when it is estimated that the magnetic field has penetrated deeper into the metallic material M than the deepest crack depth desired to be measured in the metallic material M, the current fed by the signal generator 7 is in a second step S20 controlled by the control unit 9 such that the essentially constant current obtains a second magnitude I2. The second magnitude I2 may for example be essentially zero or zero. The second step S20 may hence involve setting the transistor in its closed state. The change of current feed from the first amplitude I1 to the second amplitude I2 causes an induced current to be generated in the metallic material M. The current which is fed by the signal generator 7 is preferably in the form of a pulse train 22a as shown in the uppermost diagram in FIG. 3a. Measurements of the magnetic field are typically taken between subsequent pulses, as will be elaborated in more detail in the following.

The estimation of when the magnetic field has penetrated deeper into the metallic material M than the deepest crack depth desired to be measured in the metallic material M may be based on theoretical estimation, with the estimated time being programmed in a software in the control unit 9 such that it can control the current output by the signal generator 7 accordingly.

The estimation may be based on when the feeding of the current to the transmitter coil 3 starts, a deepest crack depth desired to be measured, the relative permeability μ and electrical resistivity ρ of the metallic material M.

Such estimation may for instance be provided by the following relation:

$$t0-t00 > 1.5 * \mu * (CDmax)^2 / \rho,$$

where t0 is the time in milliseconds when the current obtains its second magnitude I2, as shown in FIGS. 3a and 3b, t00 is the time when the current obtains its first magnitude I1, CDmax is the maximum crack depth desired to be measured in millimeter, μ is the relative permeability of the metallic material M, and ρ is the electrical resistivity of the metallic material M in nano Ohm meter, nΩm.

Following the second step S20, the energy in the transmitter coil 3 can quickly be discharged by means of the first resistor R1 (only shown only shown in FIG. 1, incorporated into e.g. platform 20 of FIGS. 2a and 2b). The first resistor R1 is hence arranged to discharge the energy from the transmitter coil 3 when the current has attained its second magnitude I2. In one embodiment the first resistor R1 may be arranged in parallel connection with the transmitter coil 3.

In a third step S30, when the current has attained its second magnitude I2, the magnetic field created by the induced current is detected by at least the first receiver coil 5. The magnetic field detected by the first receiver coil 5 induces a signal S(t), e.g. a voltage, in the first receiver coil 5 which may be amplified by means of the amplifier 11 (only shown explicitly in FIG. 1, incorporated into component 17 of FIGS. 2a and 2b). According to the example embodiment of FIGS. 2a and 2b, the magnetic field created by the induced current is also detected by the second receiver coil 6 in an optional step S35. The magnetic field detected by the second receiver coil 6 also induces a signal, Sr(t), e.g. a voltage, in the second receiver coil 6 which may be amplified by means of an amplifier.

The amplifier 11 provides the amplified signal from at least the first receiver coil 5 to the computing arrangement 12 (only shown explicitly in FIG. 1, incorporated into component 17 of FIGS. 2a and 2b). The computing arrangement 12 is in one embodiment arranged to, in a fourth step S40, in a fifth steps S50, and in a sixth step S60 determine a first signal value St1, a second signal value St2 and a third signal value St3, respectively, of the signal. In one embodiment the control unit 9 is arranged to provide control signals to the first unit 13 for the first unit 13 to be able to determine the first signal value St1 at a first time t1, the second signal value St2 at a second time t2 and the third signal value St3 at a third time t3, as shown in FIGS. 3a and 3b.

Prior to, or concurrently with the detection of the magnetic field by the first receiver coil 5 in the third step S30, and optionally the detection of the magnetic field by the second receiver coil 6, the energy created in the first receiver coil 5 by the magnetic field is discharged by means of the second resistor R2, and the energy created in the second receiver coil 6 by the magnetic field is discharged by means of the third resistor R3. The second and third resistors R2, R3 are hence arranged to discharge the energy from the first and second receiver coils 5, 6, respectively, when the current has attained its second magnitude I2. In one embodiment the second resistor R2 is arranged in parallel connection with the first receiver coil 5, and/or the third resistor R3 is arranged in parallel connection with the second receiver coil 6.

By means of proper selection of resistance of the first resistor R1, the second resistor R2 and the third resistor R3 and a fast switching between the first magnitude I1 and the second magnitude I2 of the current, a fast discharge of the energy in the transmitter coil 3 and the first and second receiver coils 5, 6 may be achieved, thus allowing for a short time span t1-t0 before commencement of magnetic field measurements by means of the first and second receiver coils 5, 6. The first time t1 is in one embodiment at a time (from t0) at which it has been estimated that any disturbances due to control of the current to obtain the second magnitude I2 have ceased, and optionally that the induced current in the metallic material M due to control of the current to obtain the second magnitude I2 has penetrated deeper in the metallic material M than a depth corresponding to surface irregularities of the metallic material M and shallow crack depths not desired to be measured. Estimation of the time when the current has penetrated to a depth deeper than surface irregularities of the metallic material M and shallow crack depths not desired to be measured may be provided by the following relation in case crack depths and surface irregularities having a depth of less than or equal to 1 mm are not desired to be measured:

$$t1 \approx 800 * \mu/\rho,$$

where t1 is the time in microseconds, μ is the relative permeability of the metallic material M, and p is the electrical resistivity in nΩm. Similar equations can be derived depending on the minimum crack depth desired to be measured. For example, measuring on high electrical resistivity material, such as hot steel (e.g. steel at 1000 ° C.), the time of decay should be less than around 1 microsecond and the time t1 is thus selected to be 1 microsecond, or between 0.5-1 microsecond (after t0). For low resistivity material, significantly longer setting of the first time t1 can be used, e.g. according to the simplified equation:

$$t1 = 30/(\rho^{1/2})$$

where ρ is the electrical resistivity of the metallic material M in nano Ohm meter, nΩm, and t1 is in microseconds.

The third time t3 is in one embodiment at a time (after t0) at which it has been estimated that any influence of a change in radius R of the curvature of the edge E has ceased. For example, the third time t3 may for measuring on high electrical resistivity material, such as hot steel (e.g. steel at 1000 ° C.) be around 12 microseconds (e.g. with a radius R of the edge E of 2 mm). For another material, the third time t3 can be set to:

$$t3 = 12 * (1000/\rho)^{1/2}$$

where ρ is the electrical resistivity of the metallic material M in nano Ohm meter, nΩm, and t3 is in microseconds.

The second time t2 is chosen at some time between the first time t1 and the third time t3. For example, the second time t2 can be chosen at a time (after t0):

$$t2 = (((t1)^{1/2} + (t3)^{1/2})/2)^2$$

Each of the first, second and third times described herein are typically programmed in the software of the control unit 9, which can provide control signals to the computing arrangement 12, e.g. the first unit 13 to determine the first signal value St1, the second signal value St2, and the third signal value St3.

For the first time t1, the first signal value St1 is determined by means of the computing arrangement 12, for instance by the first unit 13. The first signal value St1 is typically a single signal value of the signal taken at the first time t1, but may also be a mean value of the signal in a first time range extending from −30% of t1 to +30% of t1, or an integration of the signal in the first time range. Correspondingly, for the second time t2, the second signal value St2 is determined by means of the computing arrangement 12, for instance by the first unit 13. The second signal value St2 is typically a single signal value of the signal taken at the second time t2, but may also be a mean value of the signal in a second time range extending from −30% of t2 to +30% of t2, or an integration of the signal in the second time range. Finally, for the third time t3, the third signal value St3 is determined by means of the computing arrangement 12, for instance by the first unit 13. The third signal value St3 is typically a single signal value of the signal taken at the third time t3, but may also be a mean value of the signal in a third time range extending from −30% of t3 to +30% of t3, or an integration of the signal in the third time range.

The first, second and third signal values St1, St2, St3 are provided to the second unit 15 (only shown only shown in FIG. 1, incorporated into component 17 of FIGS. 2a and 2b). first, second and third signal values St1, St2, St3 may be provided in the form of an analog signal as a voltage by means of a sample-and-hold circuit arranged in the second unit 15, or alternatively as a digital signal by means of an ND-converter arranged in the second unit 15.

The first, second and third signal values St1, St2, St3 may be provided by the second unit 15 to the third unit 16 at a fourth time t4 which is after the third time t3 but prior to the time t20 in which the measurement is repeated and a new current pules is generate by the signal generator 7, wherein the first unit 13 can be reset at a fifth time t5 after the fourth time t4, for a subsequent measurement, i.e. a determination of signal values of a subsequent current pulse. This is shown in the lowermost diagram in FIG. 3b. Thus, a current pulse may at a time t20 be fed by the signal generator 7 to the transmitter coil 3, wherein the above steps S10-S60 are repeated.

In a step S70 it is determined whether a crack is present by determining the crack depth based on the on the first, second and third signal values St1, St2, St3. The determination of the crack depth can be performed in the third unit 16 by means of determining a characteristic relation between at least two of the following combinations of signal values: the first signal value St1 and the second signal value St2; the second signal value St2 and the third signal value St3; and the first signal value St1 and the third signal value St3. The inventor has realised that the combination of characteristic relations, e.g. St1/St2 and St1/St3, or St2/St3 and St1/St3 or St1/St2, are independent of the position of the edge and the radius of the curvature of the edge, which will be further explained below. As a note, the resistivity of the material is substantially constant during the detection of the crack, and the irregulates of the surface of the metallic material does not affect the measurement with regards to the characteristics of the first time t1.

Turning to FIG. 3b, the determination of a crack and its crack depth CD is performed by comparing the characteristic relations with corresponding characteristic relations of reference signals. In FIG. 3b, a first reference signal Sa(t) has been established (theoretically or by the measurement as described above with reference to steps S10-S70 but for more times than t1, t2 and t3 in order to achieve a continuous curve) in which a crack C is present at the edge E of the metallic material M. The position of the edge E compared to a reference position, here the magnetic center MC of the first receiver coil 5, and the radius R of the curvature of the edge E may correspondingly be determined by an edge position parameter and a radius parameter, respectively. The edge position parameter and the radius parameter are for the first reference signal Sa(t) representing a normal condition, corresponding to a first edge reference value of the edge position parameter and a first reference value of the radius parameter. Moreover, the following reference signals are established and presented in FIG. 3b: a second reference signal Sb(t) is established in a step S64 (theoretically or by the measurement as described above with reference to steps S10-S60 but for more times than t1, t2 and t3 in order to achieve a continuous curve) for the same metallic material having no cracks, and with the same radius parameter and edge position parameter (i.e. the first radius reference value and the first edge reference value, respectively); a third reference signal Sc(t) is established in a step S65 (theoretically or by the measurement as described above with reference to steps S10-S60 but for more times than t1, t2 and t3 in order to achieve a continuous curve) for the same metallic material having no cracks, and with the same radius parameter (i.e. the first radius reference value) but a predetermined change of the edge position parameter relative the first edge reference value; and a fourth reference signal Sd(t) is established in a step S66 (theoretically or by the measurement as described above with reference to steps S10-S60 but for more times than t1, t2 and t3 in order to achieve a continuous curve) for the same metallic material having no cracks, and with the first edge reference value as edge position parameter, and a predetermined change of the radius parameter relative the first radius reference value. Thus, all of the reference signals may be based on at least steps S10, S20, S30, S40, S50 and S60 as presented above, but for more points in time than t1, t2 and t3 in order to achieve a continuous curve.

The independency of the position of the edge may thus be performed in step 70, and preferably in the third unit 16, by the following characteristic relations of the first, second and third signal values St1, St2, St3 for example by performing the following procedure and calculations.

First, the following characteristic relations of the second and third reference signals Sb(t), Sc(t) are set up for the first, second and third times, t1-t3:

$$Sb(t1)/Sb(t2)=Sc(t1)/Sc(t2), \text{ and}$$

$$Sb(t2)/Sb(t3)=Sc(t2)/Sc(t3).$$

Based on the above characteristic relations, the position of the edge will thus not disturb the measurement.

Sb(t1)/Sb(t2) and Sc(t1)/SC(t2) may subsequently be multiplied with a constant factor N12 in order to make such product equal to one (1) when there is no crack present in the metallic material, and with the first radius reference value for the radius parameter. Correspondingly, Sb(t2)/Sb(t3) and Sc(t2)/Sc(t3) may be multiplied with a constant factor N23 in order to make such product equal to one (1) when there is no crack present in the metallic material, and with the first radius reference value for the radius parameter.

Thus, the following relations can be set up:

$$N12*Sb(t1)/Sb(t2)-1=N12*Sc(t1)/Sc(t2)-1=0;$$

$$N23*Sb(t2)/Sb(t3)-1=N23*Sc(t2)/Sc(t3)-1=0.$$

Thus, during a measurement S(t) as described above, the following equations are set up:

$$R12=N12*S(t1)/S(t2)-1$$

$$R23=N23*S(t2)/S(t3)-1$$

Deviations from zero (0) of R12 and R23 thus indicate a change of the radius of the curvature of the edge and/or the presence and depth of a crack, independent of the position of the edge.

N12 and N23 can be determined by measurements on a reference metallic material with the same or similar electric and magnetic properties as the metallic material subject to the measurement.

As is further clear from FIG. 3b, there is a considerable difference in the first reference signal Sa(t) and the fourth reference signal Sd(t) between the first time t1 and the second time t2, at least compared to a difference between the same reference signals Sa(t), Sd(t) between the second time t2 and the third time t3. Thus, R12 will result in a relative larger difference to R23 for Sa(t) compared to R12 relative R23 for Sd(t). Based on this fact, a characteristic number CR can be determined which is independent of the edge position and the radius of the curvature of the edge:

$$CR=R12-Const1*R23$$

Const 1 can be determined e.g. based on measurements on a reference material as described above including a predetermined change of the radius parameter relative the first radius reference value, and in which CR=0 for such radius changes, or it can be determined on the metallic material subject to the crack measurement but on a portion with no cracks present, and a value of Const1 giving minimal measurement variations during the measurement. That is, the value of Const1 is selected as to give minimum variations of CR when radius R of the edge is varying. For example, if the second time t2 is determined by the above equation $t2=(((t1)^{1/2}+(t3)^{1/2})/2)^2$, Const1 is equal to, or approximately equal to, one (1).

For example, by performing the method as described above, steps S10-S60, and acknowledging that CR=0 for Sd(t) (that is Const1=R12/R23), Const1=0.91, and that Sb(t1)=1, the following resulting table based on FIG. 3b could be set up:

TABLE 1

|  | t1 | t2 | t3 | N12(=t2/t1) | N23 | R12 | R23 | CR |
|---|---|---|---|---|---|---|---|---|
| Sb(t) | 1 | 0.5 | 0.25 | 0.5 | 0.5 | 0 | 0 | 0 |
| Sc(t) | 1.5 | 0.75 | 0.375 | 0.5 | 0.5 | 0 | 0 | 0.0000 |
| Sd(t) | 1.2 | 0.55 | 0.25 | 0.5 | 0.5 | 0.090909 | 0.1 | −0.0001 |
| Sa(t) | 1.15 | 0.5 | 0.23 | 0.5 | 0.5 | 0.15 | 0.086957 | 0.0709 |

Thus, a deviation of CR from zero (0) indicates the presence of a crack (acknowledging that the value −0.0001 is approximately zero).

The crack depth, CD can subsequently be determined by the following relation:

$$CD=Const2*CR+Const3$$

where Const2 and Const3 can be determined by e.g. measurements on a reference material as described above including cracks with different crack depths, or can be determined theoretically. For example, for hot steel (steel at 1000 ° C.), and times t1-t3 as described above, Const2 will be around 100 and Const3 around 1 mm.

It should be noted that the method described in the detailed description of patent application number EP2574911A1, utilizing a first and second characteristic values, CV1, CV2 and the relations thereof in order to make the measurement independent of the distance of the transmitter coil 3 and receiver coil 5 from the surface 19 of the metallic material M, the resistivity p of the metallic material M, and possible irregularities on the surface 19 of the metallic material M, as well as the third characteristic value CV3 to determined the crack length, is here referred to as a reference and may be utilized in parallel with the disclosure presented here, to determine the presence of a crack and its crack depth distal from the edge.

According to at least one example embodiment, the first and second receiver coils 5, 6 are used to determine the position of the edge E, horizontally (i.e. along, or parallel, to the surface 19 of the metallic material) relative the arrangement 1', and the vertical distance between the surface 19 of the metallic material M and the arrangement 1', in a step S37 as described in the following. The two (amplified) time dependent signals S(t), Sr(t) as described above, i.e. for the first receiver coil 5 being S(t) and for the second receiver coil 6 being Sr(t), are fed to component 17, such as e.g. the computing arrangement 12. Here, both signals S(t) and Sr(t) are separately integrated from time t0 to time t1, both times controlled by control unit 9 as previously descried. The two integrated values of S(t140) and Sr(t140) (i.e. $\int_{t_0}^{t_1} S(t)$ and $\int_{t_0}^{t_1} Sr(t)$), and the relation thereof, are used to determine the horizontal position of the edge E relative the arrangement 1' and the vertical distance between the surface 19 of the metallic material M and the arrangement 1'. In more detail, as the first receiver coil 5 is arranged relative close the to the edge E, the integrated value of S(t1-t0) will depend on both the vertical distance between the first receiver coil 5 and the surface 19 of the metallic material, as well as the horizontal distance between the first receiver coil 5 (e.g. the magnetic centre MC) and the edge E, while the integrated value of Sr(t140) will depend only on the vertical distance between the second receiver coil 6 and the surface 19 of the metallic material (as the second receiver coil 6 is arranged distant from the edge E). Thus, the position, or horizontal distance PHor, of the edge E and the vertical distance PVer to the surface 19 of the metallic material M, in relation to the arrangement 1', or coil arrangement 18, can be determined, e.g. in the computing arrangement 12 by the ratio Sr(t1-t0)/S(t1-t0). For example, by measuring on a reference material as PHor and PVer is varied (e.g. over a plurality of steps á 1 mm), the ratio:

$$\int_{t_0}^{t_1} Sr(t) / \int_{t_0}^{t_1} S(t)$$

can be determined and the relations of PHor and PVer can be determined based on e.g. the magnetic center of the transmitter coil.

For the above mentioned measurement, the first receiver coil 5 is for example arranged with horizontal distance Dr from the edge E to the magnetic centre MC approximately half the vertical distance between the surface 19 of the metallic material and the first receiver coil 5. The second receiver coil 6 is for example arranged with a horizontal distance Ds from the edge E to a magnetic centre of the second receiver coil 6 which is larger than the vertical distance between the surface 19 of the metallic material and the second receiver coil 6.

Thus, the positioning arrangement 21 can move the platform 20 in response to the measurement of PHor and PVer, and be configured to keep PHor and PVer constant during the measurement. For large variations ins PHor and PVer (e.g. +/−3-5 mm), the measurement independency of the position of the edge and radius of the curvature of the edge may not be fulfilled. Thus, according to at least one example embodiment, the measurement independency of the position of the edge and radius of the curvature of the edge is valid for variations of PHor and PVer <+/−3 mm.

It should be understood that for embodiments having only the first receiver coil 5, it is still possible to, in a step S62 establish an edge position parameter based on the position of the edge relative a reference position, i.e. a horizontal distance from the edge E and e.g. the magnetic centre MC of the first receiver coil 5, and in a step S63 establish a radius parameter based on the radius R of the curvature of the edge E. The previously described characteristic relations are adapted to be independent of the edge position parameter and the radius parameter. However, for the absolute values of the PHor and PVer, both the first and second receiver coils 5, 6 are needed.

Crack at an edge in a metallic material, should be interpreted as a crack present in the close vicinity of the edge, e.g. a crack intersecting a geometrical diagonal axis of 45° originating from the edge into the metallic material, or a crack extending from the horizontal surface of the metallic material to the lateral, vertical, surface of the metallic material. The crack depth CD may according to one example embodiment be the distance from the surface of the metallic material to a point where the crack intersects with the geometrical diagonal axis of 45°. The measurement of a crack at the edge E is here embodied by providing the transmitter coil 3 at least partly outside of the edge E of the metallic material M, and preferably overlapping so DO/DI is between 0.1-0.4. Moreover, it should be noted that the curvature of the edge need not to be round, but way as well be edgy. In such cases, a hydraulic radius or equivalent radius may be used instead of the radius presented herein.

The inventive concept has mainly been described above with reference to a few embodiments. However, as is readily appreciated by a person skilled in the art, other embodiments than the ones disclosed above are equally possible within the scope of the invention, as defined by the appended claims. Therefore, while the invention has been described in connection with what is presently considered to be most practical and preferred embodiments, it is to be understood that the invention is not to be limited to the disclosed embodiments, but on the contrary, is intended to cover various modifications and equivalent arrangements. The order of the method steps described in the present disclosure is not constrained to that described in FIG. 4. One or several of the steps could switch places, or occur in a different order without departing from the scope of the invention. However, according to at least one example embodiment, the method steps are performed in the consecutive order described in FIG. 4.

Additionally, variations to the disclosed embodiments can be understood and effected by the skilled person in practicing the claimed inventive concept, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The invention claimed is:

1. A method of determining a crack at an edge of a metallic material, the edge having a curvature with a radius, the method comprising:

feeding a current with a first magnitude to a transmitter coil for generating a magnetic field in the metallic material, controlling the current such that it obtains a second magnitude when the magnetic field is estimated to have penetrated deeper than a deepest crack depth desired to be measured in the metallic material, detecting the magnetic field by means of a receiver coil which detected magnetic field thereby generates a signal in the receiver coil, determining a first signal value of the signal at a first time at which it has been estimated that any disturbances due to control of the current to obtain the second magnitude have ceased, and determining a second signal value of the signal at a second time after the first time and determining a third signal value of the signal at a third time after the second time and determining a possible presence of a crack and its crack depth based on the first, second and third signal values by means of determining a characteristic relation between at least two of the following combinations of signal values: the first signal value and the second signal value; the second signal value and the third signal value; and the first signal value and the third signal value, wherein the method further comprises the step of providing the transmitter coil at least partly outside of the edge of the metallic material.

2. The method according to claim 1, wherein said receiver coil is a first receiver coil and the method further comprising the steps of:

detecting the magnetic field by means of a second receiver coil, which detected magnetic field thereby generates a signal) in the second receiver coil and determining the position of the edge and the distance from a surface of the metallic material, relative the first and second receiver coils, respectively.

3. The method according to claim 1, wherein the third time is a time at which it has been estimated that any influence of a radius change of the curvature of the edge has ceased.

4. The method according to claim 1, wherein the step of determining a possible presence of a crack and its crack depth comprises comparing the characteristic relations with corresponding reference signals.

5. The method according to claim 1, further comprises the steps of:

establishing an edge position parameter based on the position of the edge relative a reference position;

establishing a radius parameter based on the radius of the curvature of the edge, wherein said characteristic relations are independent of the edge position parameter and the radius parameter.

6. The method according to claim 4, further comprises the steps of:

establishing a first reference signal for a metallic material with a crack, and with a first radius reference value of the radius parameter and a first edge reference value of the edge position parameter;

establishing a second reference signal for a metallic material having no cracks, and with the first radius reference value of the radius parameter and the first edge reference value of the edge position parameter;

establishing a third reference signal for a metallic material having no cracks, and with said first radius reference value, and a predetermined change of the edge position parameter relative the first edge reference value;

establishing a fourth reference signal for a metallic material having no cracks, and with said first edge reference value, and a predetermined change of the radius parameter relative the first radius reference value.

7. The method according to claim 6, wherein the step of determining a possible presence of a crack and its crack depth includes using the characteristic relations with corresponding signal values of the first, second, third and/or fourth reference signal.

8. The method according to claim 6, wherein the edge position parameter represents, or corresponds to, the position of the edge relative a reference position, and the radius parameter represents, or corresponds to, the radius of the curvature of the edge.

9. The method according to a claim 1, wherein the first, second and third times are separate points in time.

10. The method according to claim 1, wherein said receiver coil is a first receiver coil and the method further comprising the steps of:

detecting the magnetic field by means of a second receiver coil, which detected magnetic field thereby generates a signal in the second receiver coil, and determining the position of the edge and the distance from a surface of the metallic material, relative the first and second receiver coils, respectively.

11. The method according to claim 3, wherein the step of determining a possible presence of a crack and its crack depth comprises comparing the characteristic relations with corresponding reference signals.

12. The method according to claim 3, further comprises the steps of:

establishing an edge position parameter based on the position of the edge relative a reference position;

establishing a radius parameter based on the radius of the curvature of the edge, wherein said characteristic relations are independent of the edge position parameter and the radius parameter.

13. The method according to claim 3, wherein the first, second and third times are separate points in time.

14. An arrangement for determining a crack at an edge of a metallic material, the edge having a curvature with a radius, the arrangement comprising:

a transmitter coil arranged to generate a magnetic field in the metallic material, a receiver coil arranged to detect the magnetic field, a signal generator arranged to feed a current having a first magnitude to the transmitter coil for generating the magnetic field in the metallic material, a control unit arranged to control the signal generator such that the current obtains a second magnitude when the magnetic field is estimated to have penetrated deeper than a deepest crack depth desired to be measured in the metallic material, and a computing arrangement arranged to receive a signal created by the magnetic field detected by the receiver coil, and to determine a first signal value of the signal at a first time, the first time at which it has been estimated that any disturbances due to control of the current to obtain the second magnitude have ceased, the computing arrangement being further arranged to determine a second signal value of the signal at a second time after the first time, and to determine a third signal value of the signal at a third time after the second time, wherein the computing arrangement is further arranged to determine;

a possible presence of a crack and its crack depth based on the first, second and third signal values by means of determining a characteristic relation between at least two of the following combinations of signal values: the first signal value and the second signal value; the second signal value and the third signal value; and the first signal value and the third signal value, wherein transmitter coil, in operation, is configured to be arranged at least partly outside of the edge of the metallic material.

15. The arrangement according to claim 14, wherein the transmitter coil, in operation, is configured to be arranged at least partly inside of the edge of the metallic material.

16. The arrangement according to claim 14, wherein the computing arrangement is arranged to determine the third signal value at the third time being a time at which it has been estimated that any influence of a radius change of the curvature of the edge has ceased.

17. The arrangement according to claim 14, wherein the computing arrangement is arranged do determined the first signal value, the second signal value and the third signal value at the first time, the second time and the third time respectively, wherein the first, second and third times are separate points in time.

18. The arrangement according to claim 14, wherein the receiver coil is a first receiver coil, and the arrangement further comprises a second receiver coil, and wherein the computing arrangement is further configured to receive a signal created by the magnetic field detected by the second receiver coil, and configured to determine the position of the edge and the distance from a surface of the metallic material, relative the first or second receiver coil.

* * * * *